US005538983A

United States Patent [19]
Buxbaum et al.

[11] Patent Number: 5,538,983
[45] Date of Patent: Jul. 23, 1996

[54] METHOD OF TREATING AMYLOIDOSIS BY MODULATION OF CALCIUM

[75] Inventors: Joseph D. Buxbaum, Flushing; Paul Greengard, New York, both of N.Y.

[73] Assignee: The Rockefeller University, New York, N.Y.

[21] Appl. No.: 236,411

[22] Filed: Apr. 29, 1994

Related U.S. Application Data

[63] Continuation-in-part of Ser. No. 73,112, Jun. 7, 1993, Pat. No. 5,385,915, which is a continuation-in-part of Ser. No. 809,174, Dec. 17, 1991, Pat. No. 5,242,932, and Ser. No. 524,202, May 16, 1990, abandoned.

[51] Int. Cl.$^6$ .......................... A01N 43/16; A01N 43/42; A61K 31/47
[52] U.S. Cl. .......................... 514/313; 514/453; 514/468; 514/510; 514/691; 514/729; 514/739; 514/766
[58] Field of Search .................................. 514/313, 453, 514/468, 510, 691, 729, 739, 766

[56] References Cited

U.S. PATENT DOCUMENTS

| 5,242,932 | 9/1993 | Gandy et al. | 514/313 |
|---|---|---|---|
| 5,270,165 | 12/1993 | Van Nostrand et al. | |
| 5,276,059 | 1/1994 | Caughey et al. | |

FOREIGN PATENT DOCUMENTS

| 0457295 | 10/1990 | European Pat. Off. |
|---|---|---|

OTHER PUBLICATIONS

Mattson et al., "Altered Calcium Signaling and Neuronal Injury: Stroke and Alzheimer's Disease as Examples$^{a}$", *Annals New York Academy of Sciences*, 1–21.

Peterson et al., "Changes in Calcium Homeostasis during Aging and Alzheimer's Disease$^{a}$", *Annals New York Academy of Sciences*, 262–270.

Buxbaum et al., "Cholinergic Agonists and Interleukin 1 Regulate Processing and Secretion of the Alzheimer B/A4 Amyloid Protein Precursor", *Proc. Natl Acad. Sci. USA*, 89:10075–10078 (1992).

Khachaturian, Zaven S., "Introduction and Overview", *Annals New York Academy of Sciences*, 1–4.

Landfield et al., "Mechanisms of Neuronal Death in Brain Aging and Alzheimer's Disease: Role of Endocrine–Mediated Calcium Dyshomeostasis", *Journal of Neurobiology*, 23:1247–1260 (1992).

Landfield et al., "Phosphate/Calcium Alterations in the First Stages of Alzheimer's Disease: Implications for Etiology and Pathogenesis", *Journal of the Neurological Sciences*, 106:221–229 (1991).

Le Quan Sang et al., "Platelet Cystolic Free–Calcium Concentration is Increased in Aging and Alzheimer's Disease", *Biol. Psychiatry*, 33:391–393 (1993).

Botstein et al., "Construction of a Genetic Linkage Map in Man Using Restriction Fragment Length Polymorphisms", *Am. J. Hum. Genet.*, 32, pp. 314–331 (1980).

Buxbaum et al., "Processing of Alzheimer B/A4 amyloid precursor protein: Modulation by agents that regulate protein phosyphorylation" *Proc. Natl. Acad. Sci. U.S.A.*, 87, pp. 6003–6006 (1990).

Cole et al., "Evidence for Lysosomal Processing of Amyloid β–Protein Precursor in Cultured Cells", *Neurochem. Res.*, 14, pp. 933–939 (1989).

Cotran et al., "Robbin's Pathologic Basis of Disease", 4th ed. WB Saunders, Philadelphia (1984).

Glenner and Wong, "Alzheimer's Disease: Initial Report for the Purification and Characterization of a Novel Cerebrovascular Amyloid Protein", *Biochem Biophys. Res. Commun.*, 120 pp. 885–890 (1984).

Glenner and Wong, "Alzheimer's Disease and Down's Syndrome sharing of a Unique Cerebrovascular Amyloid Fibril Protein", *Biochem Biophys. Res. Commun.*, 122, pp. 1131–1135 (1984).

Goldgaber et al., "Characterization and Chromosomal Localization of a cDNA Encoding Brain Amyloid of Alzheimer's Disease", *Science*, 235, pp. 887–880 (1987).

Jenkins, et al. "Fine Mapping of an Alzheimer Disease–Associated Gene Encoding Beta–Amyloid Protein", *Biochem. Biophys. Res. Commun.*, 151 pp. 1–8 (1988).

Kang et al., "The precursor of Alzheimer's Disease amyloid A4 protein resembles a cell–surface receptor", *Nature* (London), 325, pp. 733–736 (1987).

Masters et al. "Amyloid plaque core protein in Alzheimer disease and Down syndrome", *Proc. Natl. Acad. Sci., U.S.A.*, 82, pp. 4245–4249 (1985).

Palmert et al., "β–amyloid protein precursor of Alzheimer disease has soluble derivatives found in human brain and cerebrospinal fluid", *Proc. Natl. Acad. Sci. U.S.A.*, 86, pp. 6338–6342 (1989).

Rosea et al., "Genetic Linkage Studies in Alzheimer's Disease (AD)", *Neurology*, 38, pp. 173 (1988).

St. George–Hyslop et al. "The Genetic Defect Causing Familial Alzheimer's Disease Maps on Chromosome 21", *Science*, 235, 885–890 (1987).

Schellenberg et al., "Absence of Linkage of Chromosome 21q21 Markers to Familial Alzheimer's Disease", *Science*, 241, pp. 1507–1510 (1988).

(List continued on next page.)

*Primary Examiner*—Nathan M. Nutter
*Attorney, Agent, or Firm*—Klauber & Jackson

[57] ABSTRACT

Various first messengers linked to phospholipase C, including acetylcholine and interleukin-1, regulate the production both of the secreted form of the amyloid protein precursor and of amyloid β-protein. Intracellular signals which are responsible for mediating these effects have now been identified, and that activation of phospholipase C may affect APP processing by either of two pathways, one involving an increase in protein kinase C and the other an increase in cytoplasmic calcium levels. The effects of calcium on APP processing appear to be independent of protein kinase C activation. The observed effects of calcium on APP processing are of therapeutic utility in the treatment of Alzheimer-type amyloidosis.

13 Claims, 6 Drawing Sheets

OTHER PUBLICATIONS

Tanzi et al., "The Amyloid β Protein Gene Is Not Duplicated in Brains from Patients with Alzheimer's Disease", *Science*, 328, pp. 156–157 (1987).

Tanzi et al., "Amyloid β Protein Gene: cDNA, mRNA Distribution, and Genetic Linkage Newar the Alzheimer Locus", *Science*, 235, pp. 880–885, (1987).

Van Broeckhoven et al., "Failure of familial Alzheimer's disease to segregate with the A4–amyloid gene in several European families", *Nature*, 328, pp. 153–155 (1987).

Vitek et al., "Absence of mutation in the β–amyloid cDNAs cloned from the brains of three patients with sporadic Alzheimer's Disease", *Mol. Brain Res.*, 4, pp. 121–131 (1988).

Weidemann et al., "Identification, Biogenesis, and Localization of Precursors of Alzheimer's Disease A4 Amyloid Protein", *Cell*, 57, pp. 115–126 (1989).

Zain et al., "Molecular cloning of amyloid cDNA derived from mRNA of the Alzheimer disease brain: Coding and noncoding regions of the fetal precursor mRNA are expressed in the cortex", *Proc. Natl. Acad. Sci., U.S.A.*, 85, pp. 929–933, (1988).

Braun, "Klink, Diagnostik and Therapil der Amyloidosen", *Med. Klin.*, 67, pp. 1271–1274 (1972).

Caporaso et al., "Chloroquine inhibits intracellular degradation but not secretion of Alzheimer β/A4 amyloid precursor protein", *Proc. Natl. Acad. Sci.*, 89, pp. 2252–2256 (1992).

Siman et al., "β–*Amyloid Precursor is a PEST Protein*", *Biochem. Biophys. Res. Comm.*, 165, pp. 1299–1304 (1989).

J. L. Biedler et al., "Morphology and Growth, Tumorigenicity, and Cytogenetics of Human Neuroblasma Cells in Cintinuous Culture", *Cancer Res.*, 33, pp. 2643–2652.

Caporaso et al., "Chloroquine Inhibits Intracellular Degradation But Not Secretion of Alzheimer β/A4 Amtloid Precursor Protein", *Proc. Natl. Acad. Sci. U.S.A.*, 87, pp. 2252–2256 (Mar. 15, 1992).

Crandall et al., "Inverse Diffusion Methods for Data Peak Separation", *Anal. Biochem., 167, pp. 15 (1987).*

Donnelly, R. J. et al., "Interleukin–1 Stimulates the Beta–Amyloid Precursor Protein Promoter", *Cell Mol. Neurobiol.*, 10, pp. 485–495, (1990).

Glenner and Wong, "Alzheimer's Disease: Initial Report of the Purification and Characterization of a Novel Cerebrovascular Amyloid Protein", *Biochem Biophys. Res. Commun.*, 120, pp. 885–890 (1984).

Glenner and Wong, "Alzheimer's Disease and Down's Syndrome sharing of a Unique Cerebrovascular Amyloid Fibril Protein", *Biochem Biophys. Res. Commun.*, 122, pp. 1131–1135 (1984).

Gardella, et al., "Intact Alzheimer Amyloid Precursor Protein (APP) is present in Platelet Membranes and is Encoded by Platelet mRNA", *Biochem. Biophys. Res. Commun.*, 173, pp. 1292–1298 (1990).

Goldgaber et al., "Interleukin 1 regulates synthesis of amyloid β–protein precursor mRNA in human endothelial cells", *Proc. Natl. Acad. Sci. USA.*, 86, pp. 7606–7610 (1989).

Griffin et al., "Brain interleukin 1 and S–100 immunoreactivity are elevated in Down syndrome and Alzheimer disease", *Proc. Natl. Acad. Sci. USA.*, 86, pp. 7611–7615 (1989).

Harlow et al., Antibodies: A Laboratory Manual (Cold Spring Harbor New York 1988).

Huttner et al., "Multiple phosphorylation sites in protein I and their differential regulation by cyclic AMP and calcium", *Proc. Natl. Acad. Sci. U.S.A.*, 76, pp. 5402–5406 (1979).

Kang et al., "The precursor of Alzheimer's Disease amyloid A4 protein resembles a cell–surface receptor", *Nature* (London), 325, pp. 733–736 (1987).

E. A. Jaffe, "Culture of Human Endothelial Cell Derived from Umbilical Veins", *J. Clin. Invest.*, 52, pp. 2745–2746.

La Frauci et al., "Characterization of 5'–End Region and the First Two Exons of the β–Protein Precursor Gene", *Biochem. Biophys. Res. Commun.*, 159, pp. 297–304 (1989).

Manning et al., "Identification in rodents and other species of an mRNA homologous to the human β–amyloid precursor", *Brain Res.*,427, pp. 293–297 (1988).

Masters et al. "Amyloid plaque core protein in Alzheimer disease and Down syndrome", *Proc. Natl. Acad. Sci., U.S.A.*, 82, pp. 4245–4249 (1985).

Pang et al., "Protein tyrosine phosphorylation in synaptic vesicles", *Proc. Natl. Acad. Sci. U.S.A.*, 85, pp. 762–766 (1988).

R. Pinkas–Kramaraki et al., "Growth Factor–like Effects Mediated by Muscarinic Receptors in PC12M1 Cells", *J. Neurochem.*, 59(6), pp. 2158–2166 (1992).

Podlisny et al., "Gene Dosage of the Amyloid βPrecursor Protein in Alzheimer's Disease", *Science*, 238, pp. 669–671 (1987).

Price et al., "Cellular and Molecular Biology of Alzheimer's Disease", *Bio. Assay*, 10, pp. 67–71 (1989).

Sisodia et al., "Evidence that β–Amyloid Protein in Alzheimer's Disease Is Not Derived by Normal Processing", *Science*, 248, pp. 492–495 (1980).

R. P. Smith et al., "Platelet Coagulation Factor XI–Inhibitor, a Form of Alzheimer Amyloid Precursor Protein", *Science*, 248[a], pp. 1126–1128 (1990).

St. George–Hyslop et al. "The Genetic Defect Causing Familial Alzheimer's Disease Maps on Chromosome 21", *Science*, 235, pp. 885–890 (1987).

Tanzi et al., "The Amyloid β Protein Gene Is Not Duplicated In Brains from Patients with Alzheimer's Disease", *Science*, 238, pp. 666–669 (1987).

Warren et al., "β–Amyloid Gene Is Not Present in Three Copies of Autopsy–Validated Alzheimer's Disease", *Genomic*, 1, pp. 307–312 (1987).

Weidemann et al., "Identification, Biogenesis, and Localization of Precursors of Alzheimer's Disease A4 Amyloid Protein", *Cell*, 57, pp. 115–126 (1989).

Yamada et al., "Structure and Expression of the Alternatively–Spliced Forms of mRNA for the Mouse Homolog of Alzheimer's Disease Amyloid Beta Protein Precursor", *Biochem. Biophys. Res. Commun.*, 158, pp. 906–912 (1987).

5,538,983

METHOD OF TREATING AMYLOIDOSIS BY MODULATION OF CALCIUM

This work was supported by United States Public Health Service Grants AG09464 and AG10491. The Government may have certain rights therein.

CROSS-REFERENCE TO RELATED APPLICATIONS

The present application is a Continuation-In-Part of U.S. Ser. No. 08/073,112, filed Jun. 7, 1993 and now U.S. Pat. No. 5,305,915, which is a Continuation-In-Part of U.S. Ser. No. 07/809,174, filed Dec. 17, 1991, now U.S. Pat. No. 5,242,932 and Continuation-in-part of U.S. Ser. No. 07/524,202, filed May 16, 1990 and now abandoned. The disclosures thereof are incorporated herein by reference.

BACKGROUND OF THE INVENTION

Alzheimer disease is characterized by distinct neuropathological lesions, including intracellular neurofibrillary tangles, extracellular parenchymal and cerebrovascular amyloid deposits, and selective cell death that particularly affects cholinergic neurons in the basal forebrain. The principal component of parenchymal amyloid plaque cores and cerebrovascular amyloid is the amyloid β-protein (Aβ). It has been shown that this ~4-kDa protein is produced by various cultured cells including transfected cells stably expressing the amyloid protein precursor (APP), from which Aβ is derived.

During the past few years, a variety of evidence has emerged indicating that the processing of APP is regulated by signal transduction pathways. Thus, phorbol esters (activators of protein kinase C) and okadaic acid (an inhibitor of protein phosphatases 1 and 2A) increase APP metabolism and secretion. More recently, it has been shown that first messengers known to activate the phospholipase C/protein kinase C cascade increase the secretion of APP. It has also been shown that the formation of a peptide with properties similar to those of Aβ was decreased by phorbol esters, by okadaic acid, by direct activators of phospholipase C, and by first messengers that activate phospholipase C. However, activation of phospholipase C not only activates protein kinase C (through the formation of diacylglycerol, DAG) but also increases cytoplasmic calcium levels (through the action of inositol triphosphate, $IP_3$). For this reason, it was important to determine whether the $IP_3$/calcium limb of this pathway might, like the DAG/protein kinase C limb, affect APP processing.

SUMMARY OF THE INVENTION

The present invention is concerned with a method of utilizing agents that modulate cytoplasmic calcium levels, thereby affecting the metabolism of APP. Using various of the proteins found in extracellular amyloid plaques of mammalian cells as a model system, Applicants have observed that APP metabolism, and in particular, the production of the secreted form of APP, can be affected by agents that modulate cytoplasmic calcium levels. This modulation of cytoplasmic calcium levels results in alterations of the amount of the secreted form of APP with a corresponding change in the amount of the deposition of amyloid β-protein (Aβ) in extracellular sites characteristic of Alzheimer's disease.

The present invention thus concerns a method of increasing the secreted form of APP, e.g., introducing into a patient or into a cell of a patient, an effective amount of a calcium modulator, the modulator capable of enhancing the rate of production of the secreted form of the APP protein, thereby decreasing the production of amyloid β-protein and altering the formation of the resultant neurofibrillary tangles.

The present invention is also directed to a method of inhibiting production of Alzheimer-type amyloidosis in a mammal comprising administering to the mammal an effective amount of at least one modulator of cytoplasmic calcium levels, the modulator capable of altering the levels of the secreted form of APP, and thereby altering the production of Aβ.

The present invention also relates to a treatment of amyloidosis associated with Alzheimer's disease in a mammalian patient comprising administering to the patient an effective amount of at least one agent capable of modulating cytoplasmic calcium levels by altering the production of the secreted form of APP in mammalian cells. Further, this treatment can encompass the co-administration of an agent which affects proteolytic processing of APP by altering phosphorylation or the endolysosomal degradation of APP.

The present invention also relates to a method for screening for agents that modulate amyloid formation comprising contacting mammalian cells with an agent suspected of being capable of modulating the cytoplasmic calcium levels, and detecting alterations in the secretion of APP, and the production of Aβ.

DETAILED DESCRIPTION OF THE DRAWINGS

Figure 1:
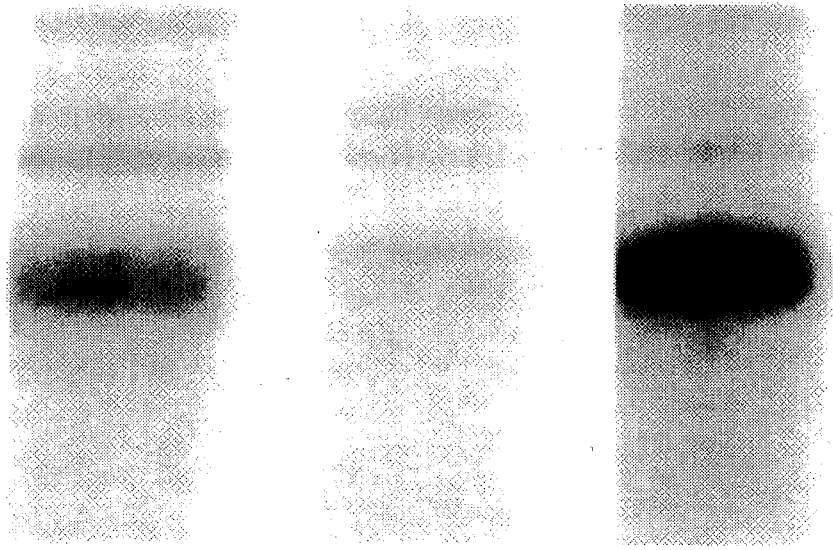
FIG. 1 is of six autoradiograms of gels from immunoprecipitates of metabolically labeled CHO cells showing the affects of various agents on secreted APP ($APP_s$) and amyloid β-protein (Aβ).
Figure 1:
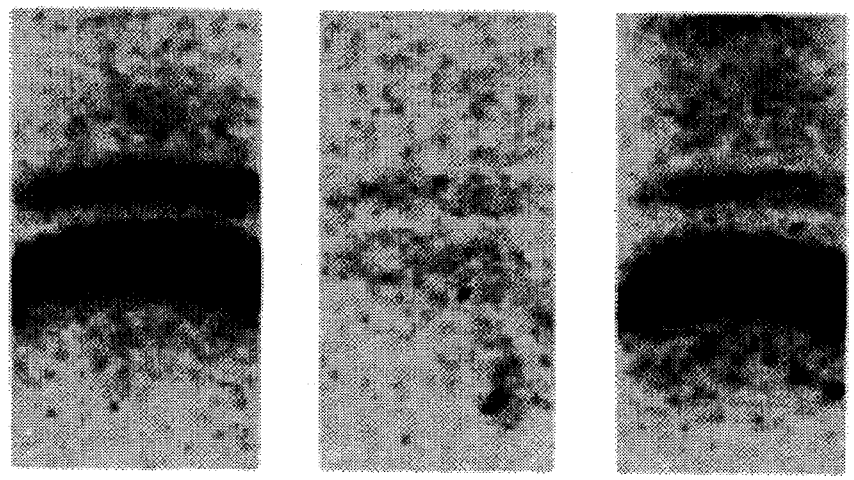

FIG. 1. Carbachol regulates formation of $APP_s$ and Aβ. $APP_s$, Aβ and p3 were immunoprecipitated from the medium of metabolically labeled CHO cells stably expressing the $M_3$ receptor. Upper panel, higher molecular weight region of a 10–20% Tris-tricine gel, showing $APP_s$ the secreted form of APP. Lower panel, lower molecular weight region of a 10–20% Tris-tricine gel, showing Aβ and p3, an Aβ fragment deleted of the first 16–17 amino acids (25). Control, no additions; $Aβ^{1-40}$, immunoprecipitation was carried out in the presence of 5 μg/ml of synthetic $Aβ^{1-40}$; Carb 1 mM carbachol.

Figure 2A:
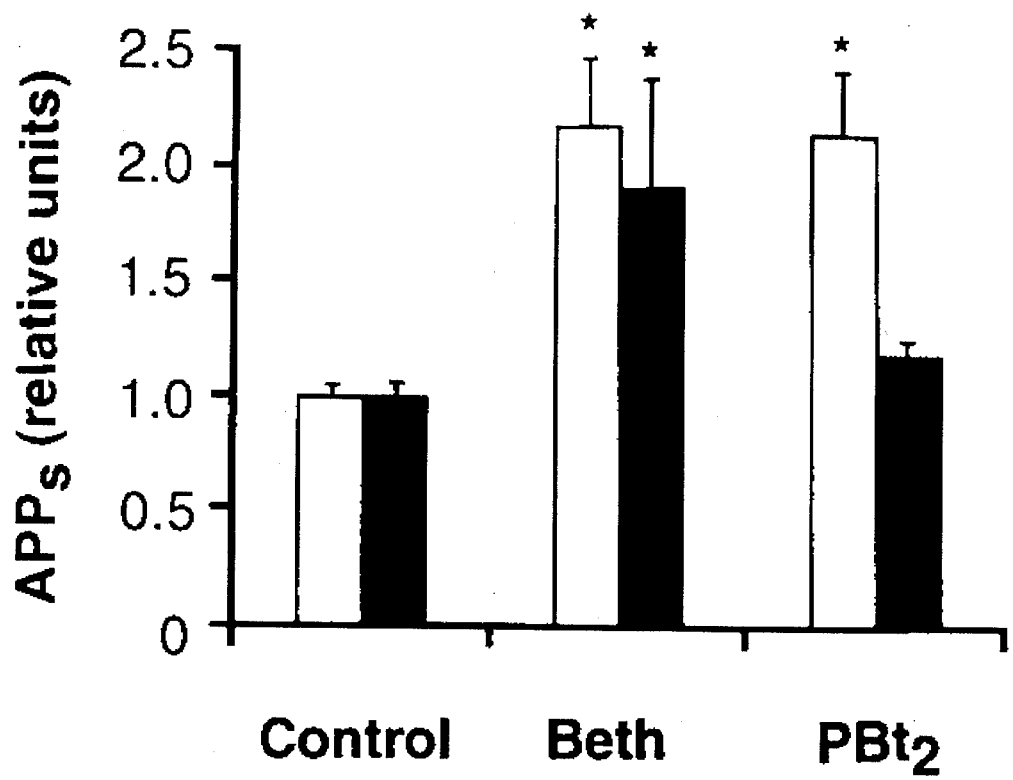
FIG. 2 is two bar graphs comparing the formation of APP, and Aβ in cells lacking functional protein kinase C when untreated or treated with either bethanechol or phorbol 12,13-dibutyrate.
Figure 2B:
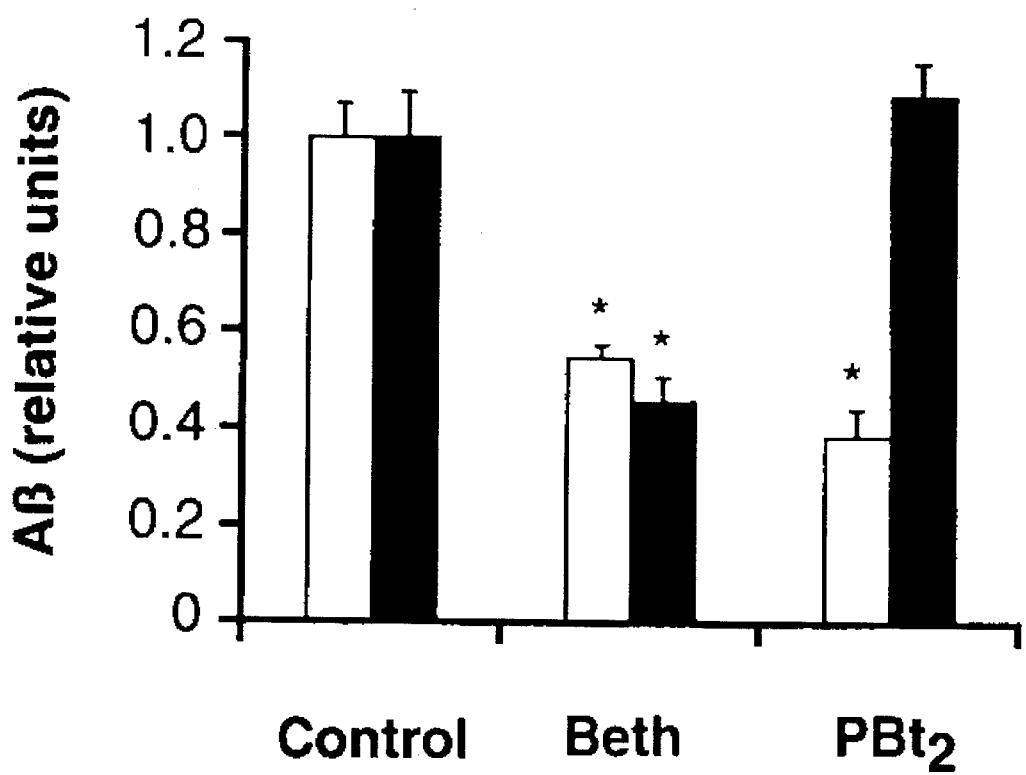

FIG. 2. Bethanechol regulates formation of $APP_s$ and $A\beta$ in cells lacking functional protein kinase C. CHO—$M_3$ cells, transiently expressing $APP_{751}$, were either untreated (open bars) or treated for 17 hours with 1 μM phorbol 12, 13-dibutyrate ($PBt_2$) to down-regulate protein kinase C (solid bars), before the start of the metabolic labeling. After metabolic labeling, $APP_s$ and $A\beta$ were immunoprecipitated from the medium. Control, no additions; Beth, 1 mM bethanechol; $PBt_2$, 1 μM $PBt_2$. *, Different from control (P<0.003).

Figure 3A:
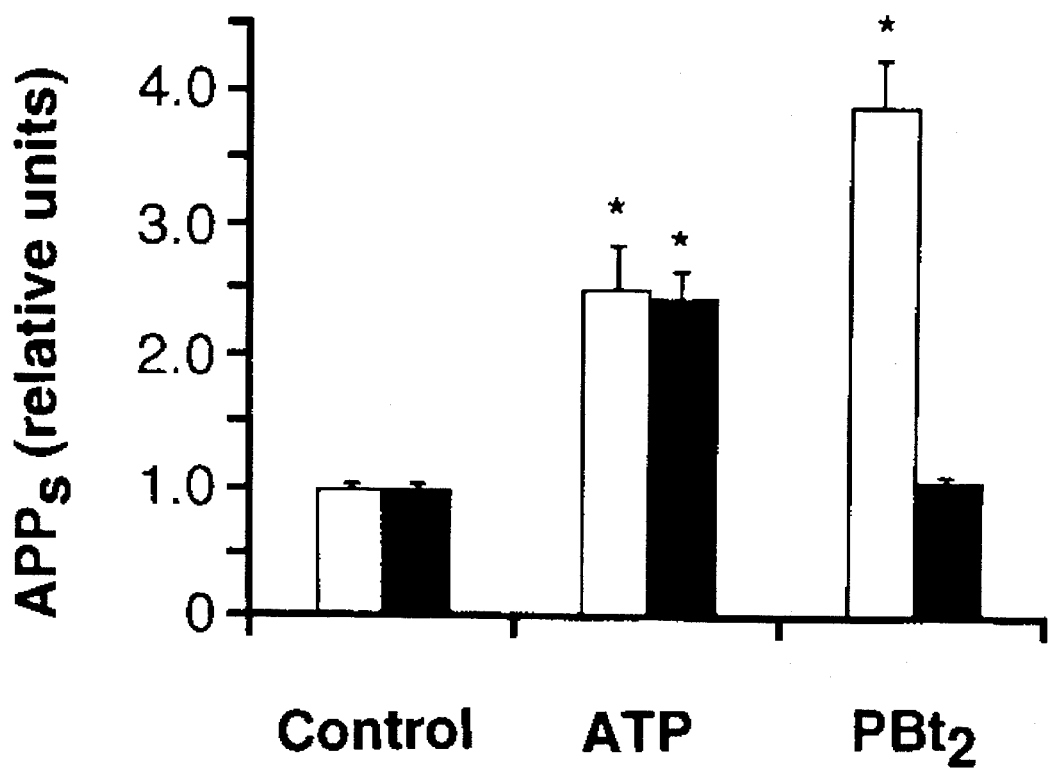
FIG. 3 is two bar graphs comparing the formation of APP, and Aβ in cells lacking functional protein kinase C when untreated or treated with either ATP or phorbol 12,13-dibutyrate.
Figure 3B:
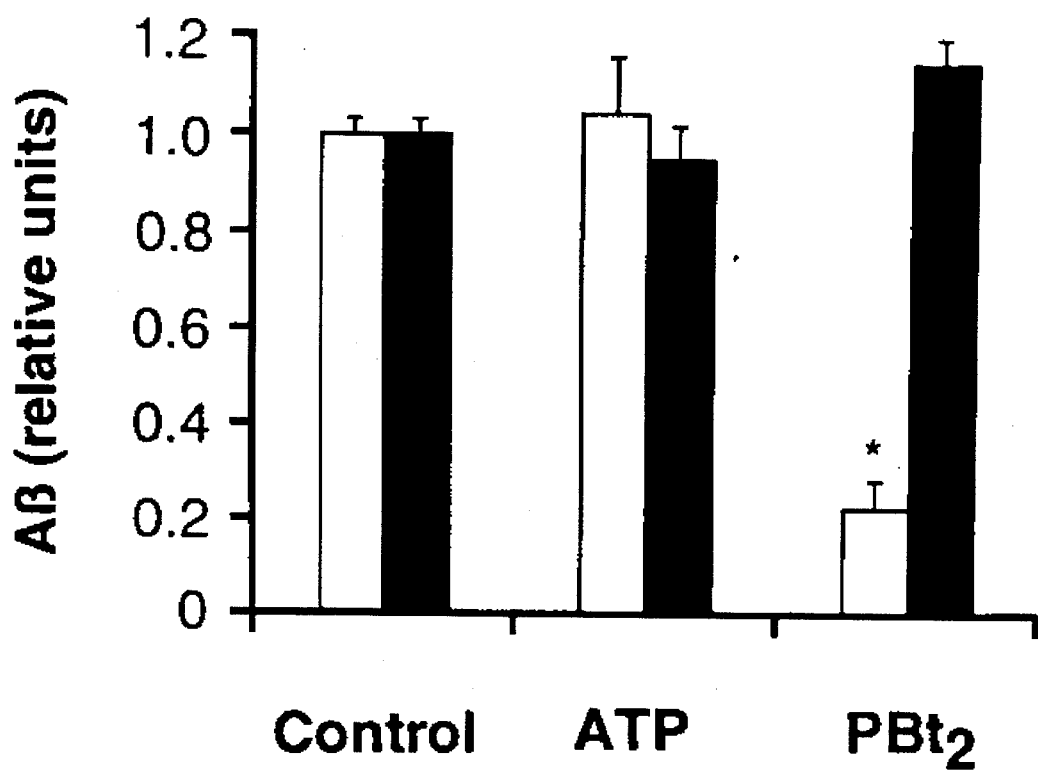

FIG. 3. ATP regulates formation of $APP_s$ and $A\beta$ in cells lacking functional protein kinase C. CHO—$APP_{751}$ cells were either untreated (open bars) or treated for 17 hrs with 1 μM $PBt_2$ to down-regulate protein kinase C (solid bars), before the start of the metabolic labeling. After metabolic labeling $APP_s$ and $A\beta$ were immunoprecipitated from the medium. Control, no additions; ATP, 1 mM ATP; $PBt_2$, 1 μmM $PBt_2$. *, Different from control (P<0.0001).

Figure 4A:
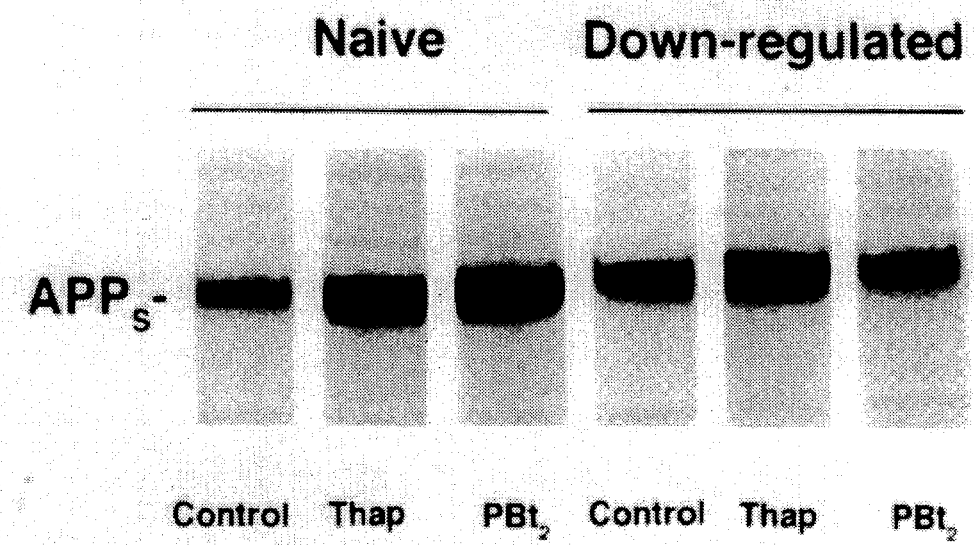
FIG. 4 is a bar graph comparing the formation of APP, in naive or down-regulated protein kinase C cells when untreated or treated with thapsigargin or phorbol 12,13-dibutyrate.
Figure 4B:
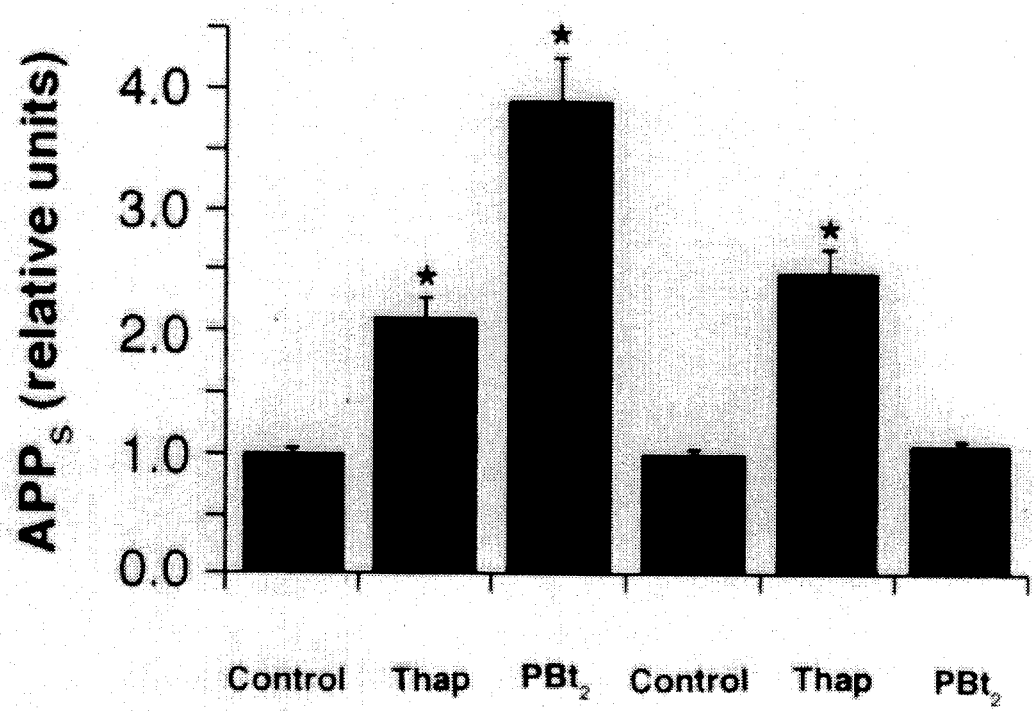

FIG. 4. Thapsigargin, a compound which raises cytoplasmic calcium levels, regulates formation of $APP_s$ in cells lacking functional protein kinase C. CHO—$APP_{751}$ cells were either untreated (naive) or treated for 17 hours with 1 μM $PBt_2$ to down-regulate protein kinase C (down-regulated), before the start of the metabolic labeling. After metabolic labeling, $APP_s$ was immunoprecipitated from the medium. Upper panel, higher molecular weight region of a 10–20% Tris-tricine gel. Lower panel, quantitation of $APP_s$. Control, no additions; Thap, 20 nM thapsigargin; $PBt_2$, 1 μM $PBt_2$. *, Different from control (P<0.0001).

Figure 5:
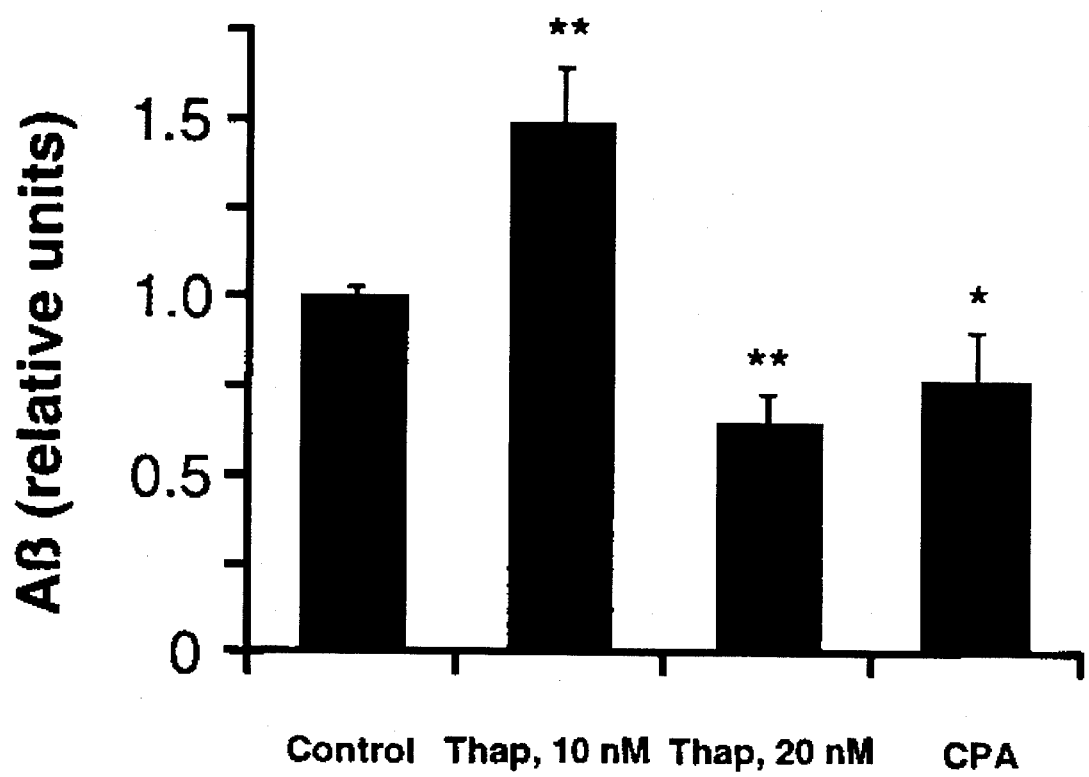
FIG. 5 is a bar graph that compares the formation of Aβ in the presence or absence of agents which raise cytoplasmic calcium levels.

FIG. 5. Agents which raise cytoplasmic calcium levels regulate formation of $A\beta$. $A\beta$ was immunoprecipitated from the medium of metabolically labeled CHO—$APP_{751}$ cells. Control, no additions; Thap, thapsigargin; CPA, cyclopiazonic acid. **, Different from control (P<0.0005); *, Different from control (P<0.05).

Figure 6:
FIG. 6 is an autoradiogram of a gel from immunoprecipitates of metabolically labeled HTB148 cells showing the effects of various agents on secreted APP ($APP_s$).

FIG. 6. Regulation of formation of $APP_s$ in human neuroglioma cells. $APP_s$ was immunoprecipitated from the medium of metabolically labeled HTB 148 cells. The higher molecular weight region of a 10–20% Tris-tricine gel is shown. Control, no additions; Thap, 20 nM thapsigargin; $A\beta^{1-40}$, immunoprecipitation was carried out in the presence of 5 μg/ml of synthetic $A\beta^{1-40}$; Carb, 1 mM carbachol; IL-1, 100 U/ml interleukin-1; $PBt_2$, 1 μM $PBt_2$.

DETAILED DESCRIPTION OF THE INVENTION

Phospholipase C (PLC) activation can affect APP processing via either of two pathways.

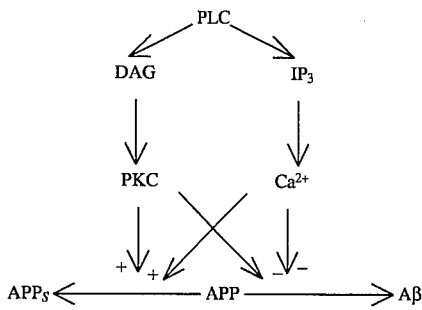

Activation of phospholipase C regulates formation of $APP_s$ and $A\beta$ via two distinct mechanisms.

Phospholipase C (PLC) hydrolyzes phosphoinositol bisphosphate yielding two intracellular signaling molecules, DAG and $IP_3$. DAG activates protein kinase C (PKC), which enhances $APP_s$ production and diminishes $A\beta$ production. $IP_3$ stimulates the release of calcium from intracellular stores, which enhances $APP_s$ production and, at least under certain conditions, diminishes $A\beta$ production. The present invention utilizes this modulation by calcium levels to effect changes in APP metabolism.

The results further suggest that various ligand-operated ion channels and voltage-operated ion channels that control intracellular calcium levels may also regulate APP processing. This idea is supported by recent studies of the effects of a calcium ionophore on $APP_s$ production in cultured cells. Both $APP_s$ and $A\beta$ have been demonstrated to modulate intracellular calcium levels, raising the possibility, when taken together with the data presented here, that these compounds may regulate their own formation.

The present invention utilizes various modulators of cytoplasmic calcium levels to modulate the secreted form of APP ($APP_s$), thereby affecting or modulating the formation of amyloid deposits, particularly in Alzheimer's disease.

The following is a list of known agents which can be utilized in the present invention to modulate cytoplasmic calcium levels thereby changing the levels of the corresponding $APP_s$ and $A\beta$ formation.

This listing is not meant to be a complete or exhaustive list, but is representative of the modulators useful in the methods of the present invention.

thapsigargin;

cyclopiazonic acid;

phorbol esters, such as phorbol 12,13-dibutyrate and phorbol 12-myristate 13-acetate;

carbachol; and interleukin-1.

It is to be understood that derivatives of the above modulators are encompassed by the present invention.

Thapsigargin, a compound which elevates cytoplasmic calcium levels by irreversibly inhibiting the uptake of calcium into the endoplasmic reticulum, at higher concentrations, decreased the formation of $A\beta$ in CHO cells as well as in HaTB 148 cells. Similarly, cyclopiazonic acid, a compound which elevates cytoplasmic calcium levels by reversibly inhibiting the uptake of calcium into the endoplasmic reticulum, decreased the formation of $A\beta$ in CHO cells. These data support the idea that the ability of bethanechol to decrease $A\beta$ formation in CHO—$M_3$ cells without functional protein kinase C is mediated by calcium. In contrast, thapsigargin, at lowest concentrations, caused a small increase in the formation of $A\beta$ in CHO cells. The effect of low levels of thapsigargin on the production of $A\beta$ raises the possibility that, under some conditions in some cells, first messengers may stimulate $A\beta$ production. However, as mentioned above, it will be important to confirm by sequencing, the identity of the $A\beta$-like peptide observed.

The regulation of the formation of $A\beta$ is clearly of potential clinical relevance. As such, the role of calcium as a key regulator in this process has important therapeutic implications. Calcium has been implicated in aging and in Alzheimer disease. Utilizing calcium in therapies in $A\beta$-amyloidosis would be advantageous over attempts to regulate protein kinase C activity because, unlike protein kinase C, intracellular calcium levels do not seem to affect APP transcription. The possible physiological relevance of the calcium regulation of APP processing is supported by the studies on neuroglioma cells (HTB 148), which indicate that calcium and phospholipase C-linked first messengers can regulate APP processing in this human cell line.

The active compounds for use in the present invention can be, and are preferably, administered as a medicament, i.e., a pharmaceutical composition.

The pharmaceutical compositions used in the methods of this invention for administration to animals and humans comprise an active compound in combination with a pharmaceutical carrier or excipient.

The medicament can be in the form of tablets (including lozenges and granules), dragees, capsules, pills, ampoules or suppositories comprising the compound of the invention.

"Medicament" as used herein means physically discrete coherent portions suitable for medical administration. "Medicament in dosage unit form" as used herein means physically discrete coherent units suitable for medical administration, each containing a daily dose or a multiple (up to four times) or a sub-multiple (down to a fortieth) of a daily dose of the active compound of the invention in association with a carrier and/or enclosed within an envelope. Whether the medicament contains a daily dose, or, for example, a half, a third or a quarter of a daily dose will depend on whether the medicament is to be administered once, or, for example, twice three times or four times a day, respectively.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount, i.e., such that a suitable effective dosage will be consistent with the dosage form employed in single or multiple unit doses. The exact individual dosages, as well as daily dosages, will, of course, be determined according to standard medical principles under the direction of a physician or veterinarian.

The active compound can also be administered as suspensions, solutions and emulsions of the active compound in aqueous or non-aqueous diluents, syrups, granulates or powders.

Diluents that can be used in pharmaceutical compositions (e.g., granulates) containing the active compound adapted to be formed into tablets, dragees, capsules and pills include the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agar-agar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (h) adsorptive carriers, e.g., kaolin and bentonite; (i) lubricants, e.g., talc, calcium and magnesium stearate and solid polyethylene glycols.

The tablets, dragees, capsules and pills comprising the active compound can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, from polymeric substances or waxes.

The active ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g., cocoa oil and high esters, (e.g., $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200, except in the presence of a surface-active agent), such as solvents, dissolving agents and emulsifiers. Specific non-limiting examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil, glycerol, tetrahydrofurfuryl alcohol, polyethylene glycols and fatty acid esters of sorbitol or mixtures thereof.

For parenteral administration, solutions and suspensions should be sterile, e.g., water or arachis oil contained in ampoules and, if appropriate, blood-isotonic.

The pharmaceutical compositions which are suspensions can contain the usual diluents, such as liquid diluents, e.g., water, ethyl alcohol, propylene glycol, surface active agents (e.g., ethoxylated isostearyl alcohols, polyoxyethylene sorbitols and sorbitan esters), microcrystalline cellulose, aluminum methahydroxide, bentonite, agar-agar and tragacanth, or mixtures thereof.

The pharmaceutical compositions can also contain coloring agents and preservatives, as well as perfumes and flavoring additions (e.g., peppermint oil and eucalyptus oil, and sweetening agents, (e.g., saccharin and aspartame).

The pharmaceutical compositions will generally contain from 0.5 to 90% of the active ingredient by weight of the total composition.

In addition to the active compound, the pharmaceutical compositions and medicaments can also contain other pharmaceutically active compounds.

Any diluent in the medicaments of the present invention may be any of those mentioned above in relation to the pharmaceutical compositions. Such medicaments may include solvents of molecular weight less than 200 as the sole diluent.

It is envisaged that this active compound will be administered perorally, parenterally (for example, intramuscularly, intraperitoneally, subcutaneously, transdermally or intravenously), rectally or locally, preferably orally or parenterally, especially perlingually, or intravenously.

The dosage rate, e.g., 0.05 to 20 mg/kg of body weight, will be a function of the nature and body weight of the human or animal subject to be treated, the individual reaction of this subject to the treatment, type of formulation in which the active ingredient is administered, the mode in which the administration is carried out and the point in the progress of the disease or interval at which it is to be administered. Thus, it may in some case suffice to use less than a minimum dosage rate, while other cases an upper limit must be exceeded to achieve the desired results. Where larger amounts are administered, it may be advisable to divide these into several individual administrations over the course of the day.

The therapeutic methods of the present invention also contemplate the use of more than one of the agents of the present invention which modulate the cellular trafficking and proteolytic processing of APP in differing ways. Such combinations thus may involve, for instance, an agent which affects the intra $\beta/A_4$ cleavage, e.g., a PKC stimulator, such as interleukin 1, interleukin 6, thrombin, phorbol ester, phorbol 12,13-dibutyrate, along with an agent which affects the endolysomal degradation, e.g., chloroquine. Such agents are known from parent application U.S. Ser. No. 07/809,174. This combination has the advantages of a cumulative therapeutic effect in modulating the processing of APP, thus resulting in a reduction in the production of $\beta/A_4$ peptide production, and a concomitant reduction in amyloid formation.

The diagnostic methods of the present invention involve the screening for agents that modulate APP processing and β/A₄ peptide production, and hence amyloid formation. The invention will be further described by the examples below.

EXAMPLE 1

Materials and Methods

Cell culture conditions and the sources of analytical reagents have been described previously [Buxbaum et al. (1992). *Proc. Natl. Acad. Sci. USA* 89:10075–8 and Buxbaum et al. (1992). *Proc. Natl. Acad. Sci. USA* 90:9195–8]. HTB 148 (H4 neuroglioma) cells and CHO cells, stably transfected with either $M_1$ or $M_3$ muscarinic receptors, were purchased from ATCC. CHO cells, stably transfected with $APP_{751}$, were the gift of Dr. E. H. Koo. Transient transfection of cells with cDNA coding for $APP_{751}$ (the gift of Dr. E. H. Koo) were carried out using Lipofectin (GIBCO BRL) following the manufacturer's guidelines. Antibodies 4G8 and 6E10 were supplied by Drs. H. Wisniewski and K. S. Kim.

Pulse-chasing labeling of cells was carried out on confluent cell monolayers in 6-well culture dishes (Corning) with 1 ml of methionine-free DMEM, supplemented with 1 mCi of [$^{35}$S] methionine (EXPRE$^{35}$S$^{35}$S, NEN). Metabolic labeling was carried out for 2 hrs, followed by a chase period of 2 hrs. The chase was initiated by replacing the labeling medium with DMEM containing excess unlabeled methionine. Two minutes after the start of the chase, the indicated test compounds were added to maximize the probability that any observed effects were attributable to changes in APP metabolism rather than APP transcription. Following incubation, conditioned medium was collected and centrifuged for 5 minutes at 10,000×g. $APP_s$ and Aβ were immunoprecipitated from the conditioned medium using a mixture of two monoclonal antibodies (4G8 and 6E10). Immunoprecipitated APP fragments were subjected to SDS-PAGE on 10–20% Tristricine gels, autoradiographed and quantified using a PhosphorImager (Molecular Dynamics, Sunnyvale, Calif.). Results presented are means±SEM of 3 or more experiments performed in triplicate. ANOVA followed by Fisher's post hoc analysis was used to determine the significance of observed differences.

Results

CHO cells stably transfected with cDNA encoding either the $M_1$ (CHO—$M_1$ or the $M_3$ (CHO—$M_3$) muscarinic acetylcholine receptor were transiently transfected with cDNA encoding the 751-amino-acid isoform* of APP ($APP_{751}$). When these cells were metabolically labeled and the medium subjected to immunoprecipitation with a mixture of two antibodies (4G8 and 6E10) raised against a synthetic peptide corresponding to the first 24 residues of Aβ ($Aβ^{1-24}$), three major bands were; observed (See FIG. 1). In the higher molecular weight region of the gel, a major band with an apparent molecular mass of 130 kDa was observed, while in the lower molecular weight region of the gel, two small peptides with apparent molecular masses of 3 and 2 kDa were observed. The monoclonal antibody 6E10, which recognizes an epitope around amino acid 11 of Aβ, immunoprecipitated the 130 kDa protein and the 3 kDa peptide, but not the 2 kDa peptide (data not shown). The monoclonal antibody 4G8, which recognizes an epitope within amino acids 17–24 of Aβ, immunoprecipitated the 3 and 2 kDa peptide, but not the 130 kDa protein (data not shown). None of these three proteins were recovered when immunoprecipitation was carried out in the presence of synthetic $Aβ^{1-40}$ (See FIG. 1.)

The immunochemical properties of these three proteins, their apparent molecular weights, and the fact that they were preferentially observed in cells transiently transfected with cDNA encoding $APP_{751}$ (data not shown), allows tentative assignment as follows: the 130 kDa protein corresponds to the portion of APP which is secreted ($APP_s$), the 3 kDa peptide represents an Aβ-like peptide, and the 2 kDa peptide represents a p3-like peptide. Aβ-like peptides are heterogeneous in many cells; therefore the identify of the two low molecular weight bands awaits amino acid sequencing to determine their precise composition.

The levels of $APP_s$ increased significantly when cells expressing either the $M_1$ or $M_3$ receptor were incubated with the cholinergic agonist, carbachol (See FIG. 1 and Table 1 below;). At the same time, production of Aβ decreased dramatically (See FIG. 1, and Table 1 below;). Similarly, incubating CHO—$M_3$ cells with the muscarinic agonist bethanechol stimulated $APP_s$ production and decreased Aβ production (See FIG. 2).

TABLE 1

Phospholipase C-linked first messengers regulate formation of $APP_s$ and Aβ in CHO cells.

| Condition | $APP_s$, Relative Units | Aβ, Relative Units |
| --- | --- | --- |
| CHO—$M_1$ Cells | | |
| Control | 1.00 ± 0.07 | 1.00 ± 0.10 |
| Carbachol (1 mM) | 2.10 ± 0.17* | 0.55 ± 0.12* |
| CHO—$M_3$ Cells | | |
| Control | 1.00 ± 0.05 | 1.00 ± 0.07 |
| Carbachol (1 mM) | 1.97 ± 0.30* | 0.49 ± 0.07* |

$APP_s$ and Aβ were immunoprecipitated from the medium of metabolically labeled CHO cells which had been transiently transfected with $APP_{751}$. *, Different from control (P<0.005).

Activation of $M_1$ or $M_3$ receptors stimulates phospholipase C activity in various cells, leading to protein kinase C as well as the release of calcium from intracellular stores. The effects of activators of phospholipase C on $APP_s$ and Aβ levels might therefore arise from either the activation of protein kinase C or the activation of other calcium-dependent processes. Consistent with previous results, incubating CHO—$M_1$ cells or CHO—$M_3$ cells with phorbol 12,13-dibutyrate ($PBt_2$), a compound which activates protein kinase C, resulted in increased production of $APP_s$ and decreased production of Aβ (e.g., FIG. 2). This suggests that activation of protein kinase C following phospholipase C activation is sufficient to mediate the effects of muscarinic agonists on APP processing. To test whether activation of protein kinase C is necessary for muscarinic regulation of APP processing, we incubated CHO—$M_3$ cells, transiently expressing $APP_{751}$, for 17 hours. in 1 μM $PBt_2$ which leads to the down-regulation of protein kinase C. Under these conditions, bethanechol still increased the formation of $APP_s$ and decreased Aβ formation even though $PBt_2$ was no longer effective (FIG. 2). These results support the possibility that bethanechol and other phospholipase C activators may affect the formation of $APP_s$ and Aβ through an action on the $IP_3$/calcium pathway.

Incubation of CHO—$APP_{751}$ cells with the phospholipase C-linked first messenger ATP stimulated $APP_s$ formation.

This effect was also observed after down-regulation of protein kinase C (See FIG. 3). ATP had no effect on Aβ production under conditions in which it stimulated APP$_s$ secretion, suggesting that APP is not limiting for the formation of Aβ under these conditions.

EXAMPLE 2

To evaluate further the possibility that changes in intracellular calcium levels are sufficient to mediate the effects of phospnolipase C on APP processing, we incubated CHO—APP$_{751}$ cells with thapsigargin, a compound which elevates cytoplasmic calcium levels by irreversibly inhibiting the uptake of calcium into the endoplasmic reticulum. Incubation of cells with 20 nM thapsigargin as described in Example 1 led to a dramatic increase in APP$_s$ production (See FIG. 4). A study of the effects of various concentrations of thapsigargin on APP$_s$ production demonstrated an EC$_{50}$ value of ca.8 nM (data not shown).

In order to ascertain whether the effect of thapsigargin on APP$_s$ formation was due to activation of protein kinase C, we down-regulated protein kinase C by incubating CHO—APP$_{751}$ cells with 1 μM PBt$_2$ for 17 hours before carrying out metabolic labeling. Incubating such cells with thapsigargin led to increased APP$_s$ production which was indistinguishable from that observed in naive cells, whereas PBt$_2$ no longer had an effect on the treated cells (FIG. 4).

Experiments similar to those using thapsigargin were carried out using cyclopiazonic acid (CPA) which elevates cytoplasmic calcium levels by reversibly inhibiting the uptake of calcium into the endoplasmic reticulum. Incubation of naive CHO—APP$_{751}$ cells with 10 μM CPA stimulated APP$_s$ production, resulting in a 3.9±0.74 fold increase in APP$_s$ recovered in the medium. Incubation of protein kinase C-down-regulated CHO—APP$_{751}$ cells with 10 μM CPA resulted in a 3.1±0.45 fold increase in APP$_s$ production.

In contrast to the effect of thapsigargin on APP$_s$ production, which was stimulatory at all concentrations tested (5 nM and above), its effect on Aβ production depended qualitatively on the concentration used. Thus, Aβ production was increased in the presence of 10 nM thapsigargin and decreased in the presence of 20 nM thapsigargin (FIG. 5). CPA, used at a 10 μM concentration, decreased Aβ production (See FIG. 5).

The effects of phospholipase C activators, of thapsigargin, and of PBt$_2$ on APP processing were tested in a human neuroglioma (HTB 148) cell line (See FIG. 6 and Table 2 below). In this cell line, these agents increased APP$_s$ formation and decreased Aβ formation. It was not feasible to evaluate whether or not these compounds acted through protein kinase C, because incubation of these cells with PBt$_2$ under conditions which cause a down-regulation of protein kinase C results in a large up-regulation of APP transcription. The effects observed with PBt$_2$ disagree with those of a previous report in which PBt$_2$ had no affect on APP$_s$ formation but decreased Aβ formation (Gabuzda et al. (1993) *J. Neurochem.* 61:2326–9).

TABLE 2

Regulation of formation of APP$_s$ and Aβ in human neuroglioma cells by various substances.

| Treatment | APP$_s$, Relative Units | Aβ, Relative Units |
| --- | --- | --- |
| Control | 1.00 ± 0.11 | 1.00 ± 0.08 |
| Thapsigargin, 20 nM | 5.16 ± 1.35* | 0.56 ± 0.20* |
| Carbachol, 1 mM | 5.13 ± 1.18* | 0.53 ± 0.19* |
| Interleukin-1, 100 U/ml | 9.43 ± 1.34** | 0.64 ± 0.21* |
| PBt$_2$ 1 μM | 14.40 ± 2.06** | 0.37 ± 0.20* |

APP$_s$ and Aβ were immunoprecipitated from the medium of metabolically labeled HTB 148 cells. *, Different from control (P<0.05); **, Different from control (P<0.0001).

What is claimed is:

1. A method of inhibiting production of Alzheimer-type amyloidosis in a mammal comprising administering to said mammal in need of treatment an effective amount of at least one modulator of cytoplasmic calcium levels said modulator capable of altering the production of the secreted form of amyloid protein precursor.

2. A method according to claim 1 wherein the modulator is a phorbol ester.

3. A method according to claim 1 wherein the modulator is thapsigargin.

4. A method according to claim 1 wherein the modulator is cyclopiazonic acid.

5. A method according to claim 1 wherein the modulator is carbachol.

6. A method according to claim 1 wherein the modulator is interleukin-1.

7. A method of increasing the secreted form of APP comprising administering to a mammal in need of such treatment an effective amount of at least one modulator of cytoplasmic calcium levels, thereby altering the production of said secreted APP.

8. A method according to claim 7 wherein the modulator is a phorbol ester.

9. A method according to claim 7 wherein the modulator is thapsigargin.

10. A method according to claim 7 wherein the modulator is cyclopiazonic acid.

11. A method according to claim 7 wherein the modulator is carbachol.

12. A method according to claim 7 wherein the modulator is interleukin-1.

13. A method for screening for agents that modulate amyloid formation which comprises contacting mammalian cells with an agent suspected of being capable of modulating the cytoplasmic calcium levels, and detecting alterations in the secretion of APP, and the production of Aβ.

* * * * *